United States Patent [19]

Parker et al.

[11] Patent Number: 5,756,875
[45] Date of Patent: May 26, 1998

[54] THIN FILM PHANTOMS AND PHANTOM SYSTEMS

[75] Inventors: Kevin J. Parker; Daniel B. Phillips, both of Rochester, N.Y.

[73] Assignee: The University of Rochester, Rochester, N.Y.

[21] Appl. No.: 423,328

[22] Filed: Apr. 14, 1995

[51] Int. Cl.$^6$ .................................................. G01N 29/00
[52] U.S. Cl. ...................... 73/1 DV; 367/13; 128/660.01
[58] Field of Search .................. 73/1 DV, 866.4, 73/1 R, 865.6; 367/13; 434/268; 128/660.01

[56] References Cited

U.S. PATENT DOCUMENTS

| | | | |
|---|---|---|---|
| 4,277,367 | 7/1981 | Madsen et al. | 73/600 |
| 4,331,021 | 5/1982 | Lopez et al. | 73/1 DV |
| 4,406,153 | 9/1983 | Ophir et al. | 73/1 DV |
| 4,417,582 | 11/1983 | Trimmer et al. | 128/660 |
| 4,453,408 | 6/1984 | Clayman | 73/1 DV |
| 4,493,653 | 1/1985 | Robbins et al. | 73/866.4 |
| 4,843,866 | 7/1989 | Madsen et al. | 73/1 DV |
| 4,894,013 | 1/1990 | Smith et al. | 434/268 |
| 4,903,523 | 2/1990 | Flynn | 73/1 DV |
| 4,974,461 | 12/1990 | Smith et al. | 73/865.6 |
| 5,036,280 | 7/1991 | Chesavage | 324/308 |
| 5,052,934 | 10/1991 | Carey et al. | 434/268 |
| 5,054,310 | 10/1991 | Flynn | 73/1 DV |
| 5,055,051 | 10/1991 | Duncan | 434/262 |
| 5,111,310 | 5/1992 | Parker et al. | 358/456 |
| 5,315,512 | 5/1994 | Roth | 364/413.25 |
| 5,341,808 | 8/1994 | Rickey et al. | 128/660.01 |

FOREIGN PATENT DOCUMENTS 28 14 336  5/1979  Germany.

OTHER PUBLICATIONS

Translation—DT 2814336.
Phillips et al.—"A New Imaging Science Phantom for Performance Evaluation of Ultrasound Imaging Systems", pp. 1357–1360.

(List continued on next page.)

*Primary Examiner*—Hezron E. Williams
*Assistant Examiner*—Nashmiya Ashraf
*Attorney, Agent, or Firm*—M. Lukacher; K. Lukacher

[57] ABSTRACT

Phantoms for testing and measuring the performance of ultrasonic imaging systems have regions of precisely controlled scattering or echogenicity which contain sub-resolvable scatterers. The regions are precisely positioned so as to define patterns which form images from which the performance of the ultrasonic imaging system can be evaluated to assure the quality of the images. The phantoms can reveal the combined influences of all the stages in the imaging chain in terms of modulation transfer function and resolution limits as well as other artifacts and defects in the system such as aliasing and degraded frequency response which cannot be evaluated with conventional ultrasound phantoms. The subresolution scattering regions may be formed by printing them on a thin film sheet or substrate using photo lithography, electrostatic xerographic printing or etching; the toner particles or deposited material forming the scatters being sub-resolvable in size. Half-tone masks, such as blue noise masks, may be used to produce regions of precisely controlled sub-resolvable scatters to be used for grey scale evaluation of the imaging system by producing speckle images of different echogenicity. The thin film sheets are thinner than the thickness of the ultrasonic beam and enable propagation of the beam in the plane of the sheets to the patterns which may be located at different depths. The thin film sheets may be displaced, as by being vibrated. The sheets may be made of piezoelectric material having electrodes across which varying electrical signals are applied to displace the sheets thereby simulating movement of objects for Doppler measurements.

53 Claims, 13 Drawing Sheets

OTHER PUBLICATIONS

AIUM Quality Assurance Manual for Grey-Scale Ultrasound Scanners—Draft 10, Oct. 31, 1994.

Radiology Instruments and Accessories—Nuclear Associates, Catalog 6-6.

Tissue Mimicking Materials for Ultrasound Phantoms—Madsen et al Med. Phys. 5(5), Sep./Oct. 1978.

What Might Echography Earn From Image Science? C. R. Hill et al. Ultrasound in Mod. & Biol. 17, 6, 559–575, 1991.

Physical Limits to the Performance of Imaging Systems ; A. Rose et al, Physics Today, Sep. 1989, pp. 24–32.

Standard Methods for Measuring Performance of Pulse-Echo Ultrasound Imaging Equipment AIUM Standards Committee—American Institute of Ultrasound in Medicine, 1991.

Cone Instruments—New Ultrasound Catalog, vol. 15, 1993.

Multipurpose Sector Scan Phanton Model 520.

THIN FILM PHANTOMS AND PHANTOM SYSTEMS

The present invention relates to systems (methods and apparatus) for testing and measuring the performance of ultrasonic imaging systems, also known as echography systems, and to test targets for ultrasound imaging, which are often called phantoms, and enable the assessment of the performance of the ultrasonic imaging system in terms of criteria that modern imaging science has recognized as necessary or desirable for such assessment including, for example, the modulation transfer function of the system, resolution, aliasing, and spatial frequency response.

Ultrasonic imaging systems generate ultrasonic beams with pulses that are transmitted, reflected and received primarily in an axial direction. A lateral repetition of this process is referred to as a scan and provides signals that are amplified, detected and interpolated to a cartesian image space in digital scan converters. Sometimes the image signals are transmitted over communications links to a receiving station far removed from the patient where diagnoses based upon the ultrasonic images are made. It is important for medical imaging that the quality of the entire system be assessed. It therefore is desirable to have test targets or phantoms which provide images from which the performance of the entire system can be assessed.

Imaging science has developed criteria such as modulation transfer function (MTF) which can provide assessment of aliasing, spatial frequency response, and resolution limits for the evaluation of imaging systems generally. Such assessments have not been possible with conventional ultrasound phantoms. These phantoms use objects which mimic lesions of different size and echogenicity (the capacity of the target to produce sound "echoes" or reflections). Rods, spheres, cones and other geometrical objects of a size which can be resolved by the system are used in conventional phantoms and are located in volumes containing water or tissue mimicking material (such as gels). Doppler shift phantoms for velocity measurement and velocity image production use moving strings or fluids. None of these phantoms are able to produce detailed, high resolution patterns that permit accurate evaluation of MTF and other imaging science criteria which represent the performance of the imaging system. Some phantoms have been suggested which use random scatterer regions in three-dimensional space or in two-dimensions, to assess the beam width of the beam produced by the ultrasonic transducer of the system, but these phantoms have not been provided with precisely defined patterns from which imaging science criteria can be determined.

The present invention provides a system (method and apparatus) for evaluation and assessment of ultrasonic imaging systems and improved phantoms which can test the overall response and performance of the ultrasonic imaging system thereby revealing system performance with imaging science criteria, such as MTF and similar analytical assessments. The combined influence of all stages in the ultrasonic imaging system including any communication link, which is used for teleradiography, may thereby be evaluated. Further information concerning imaging science criteria may be had from C. R. Hill et al. Ultrasound in Mod. & Biol. 17, 6, 559, and A. Rose et al. Physics Today, September 1989, P.24–32.

Phantoms can be provided in accordance with the invention on thin films or sheets by conventional printing techniques, such as electrostatic or xerographic printing, as with a laser printer, thereby providing regions with precise control in local concentration, as well as distribution, of scatterers. The scatterers are of sub-resolvable size which is less than the wavelength of the ultrasonic energy. Because of the thin substrate, in the form of a planar medium on which the regions are located, insonation of the entire pattern is facilitated. This enables the production of a test image having an axial extent (vertical depth on the image display) which reveals imaging criteria, such as contrast at different depths. The echogenicity (the intensity of the echoes from the scatterers) can be precisely controlled in the formation of the regions thereby providing precisely controlled scattering, both from the regions and their positions on the substrate (the patterns of the regions). Since the actual scatterers are sub-resolvable, the ultrasound system can only detect their presence or absence, not any variability of the exact number and exact position of individual scatterers. The individual scatterers may be referred to as "digital" (either on or off, there or not there) in nature. The precise placement of these digital scatterers can then be used to create regions of controllable echogenicity based on their number per unit area and their arrangement relative to each other, similar in concept to a half-tone printing process. These patterns of regions can be analyzed with the same computer system algorithms as used in electro-optical imaging systems, thus, facilitating the measurement of the imaging science criteria, such as the Modulation Transfer Function (MTF) which is defined as the normalized ratio of the measured intensity modulation of an image relative to the known intensity modulation of the originating object as a function of spatial frequency. Intensity modulation is defined as the ratio of maximum intensity difference to the sum of the intensity level extremes Imax & Imin, i.e. Modulation=

$$\frac{Imax - Imin}{Imax + Imax}$$

The invention provides a thin-film phantom with digital scatterers in predetermined patterns. Such patterns may take the form of half-tone masks for grey scale contrast evaluation. They may be in the form of chirp and other suitable patterns for MTF and other system response criteria determination.

While electrostatic or xerographic printing is presently preferred, other techniques for making patterns on thin-film substrates including lithography, sputtering, vacuum deposition and etching may be used. The scatterers in the region are of dimensions much finer than that of a wavelength produced by the ultrasonic imaging system. For example, for a diagnostic system using a beam of energy at 5 MHz in soft tissue, one wave length corresponds to approximately 300 microns. A conventional 300 dots per inch laser printer using 10 micron toner particles can produce scatterers having a size of approximately 85 microns which are sub-resolvable in terms of the wavelength of the interrogating ultrasound beam. Thus, patterns of regions of sub-resolvable scatterers can be provided on a thin film substrate to afford phantoms for testing for different criteria. The patterns may be regularized or periodic profiles for producing frequency dependant changes in the speckle pattern of the images. Bars generated by a half-tones screen or mask, preferably a blue noise mask may be used. See Parker et al. U.S. Pat. No. 5,111,310 issued May 5, 1992 for information concerning blue noise mask generation by computer techniques.

The thin-film phantoms may be precisely displaced, preferably by utilizing a piezo electric material, such as PVDF as the substrate, across which a varying electrical field is applied by means of electrodes. The field may be sinusoidal to set up sinusoidal vibrations or may use other waveforms for other displacement characteristics which may be desired. For example, electrical waveforms such as ramps, chirps, AM signals, FM signals and even musical tones may be applied to induce displacements and produce Doppler signals in the audio range. The displacements are preferably at a vibration rate which should be less than the pulse repetition rate (PRF) of the pulses which comprise the ultrasound beam and a size which maintains the sub-resolution characteristics of the scatterers in the regions, i.e. the peak displacement should be less than one wavelength of the ultrasound.

Briefly described therefore, the invention provides a system for testing ultrasonic imaging systems which project a beam of ultrasonic energy. The beam may scan a plane to form an image of scattering objects in the plane. In accordance with the invention, different patterns of regions of sub-resolvable scatterers on planar mediums are provided. The mediums are of such an acoustic impedance characteristic that the beam propagates in and along the plane of the medium without substantial reflection or attenuation. The image formed by the scattering of the pattern is analyzed to evaluate the performance of the system, preferably utilizing imaging science criteria.

The foregoing and other features, objects and advantages of the invention as well as presently preferred embodiments thereof will become more apparent from a reading of the following description in connection with the accompanying drawings in which.

Figure 4A:
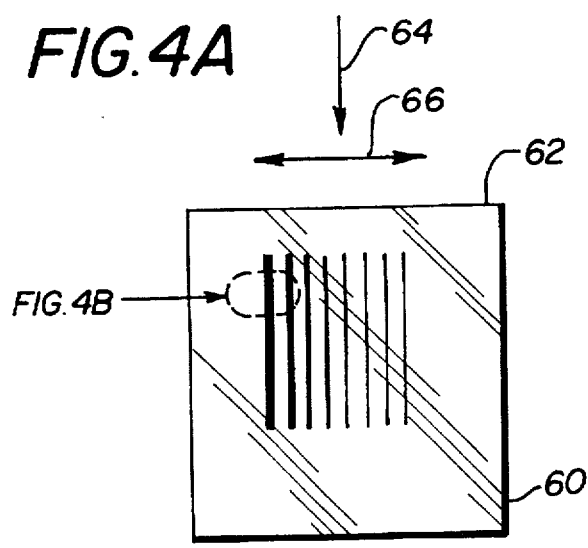
Figure 4B:
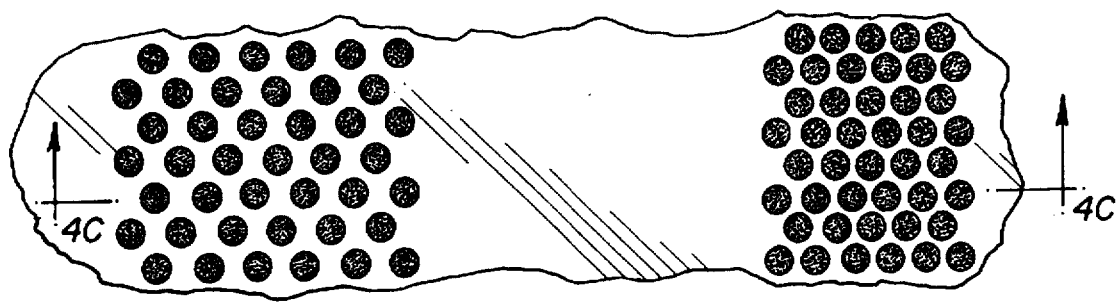
Figure 4C:
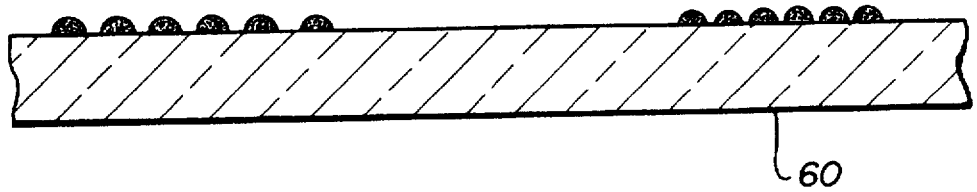
Figure 4D:
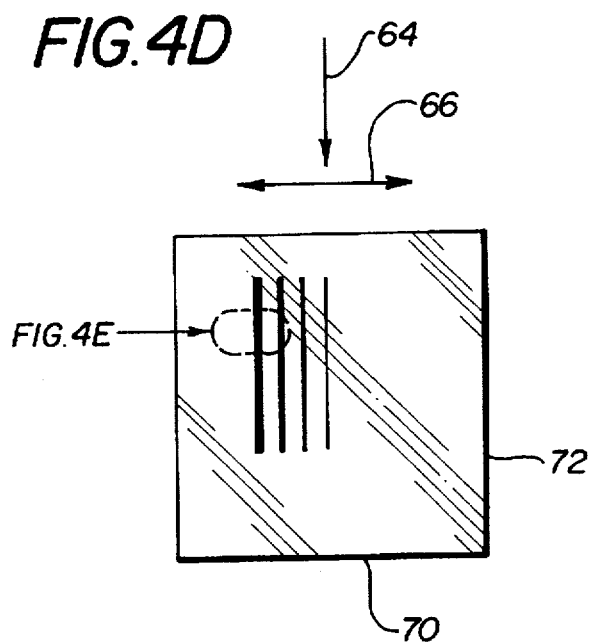
Figure 4E:
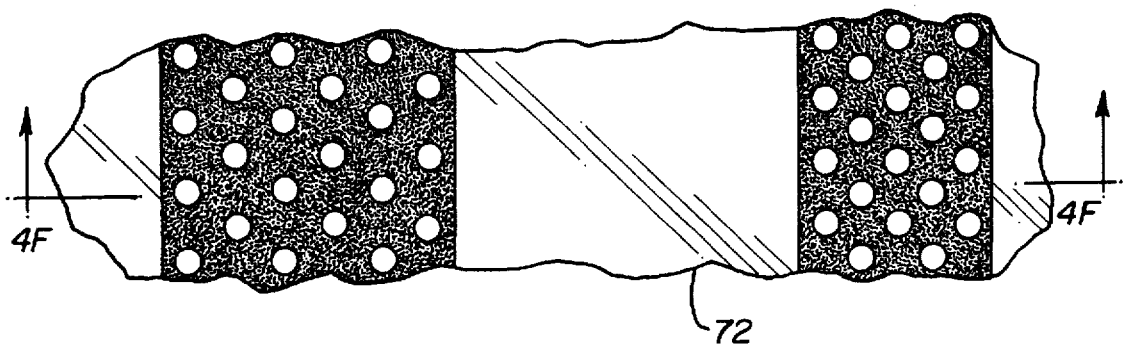
Figure 4F:
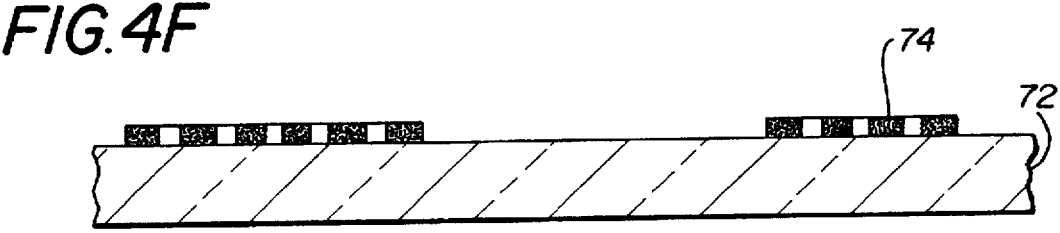
Figure 4G:
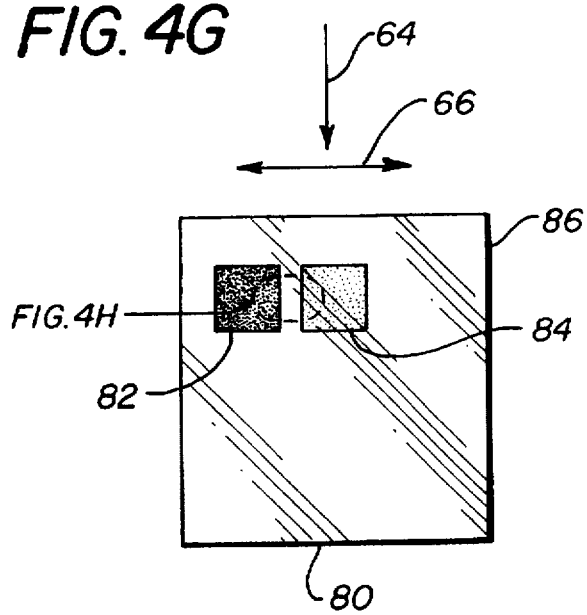
Figure 4H:
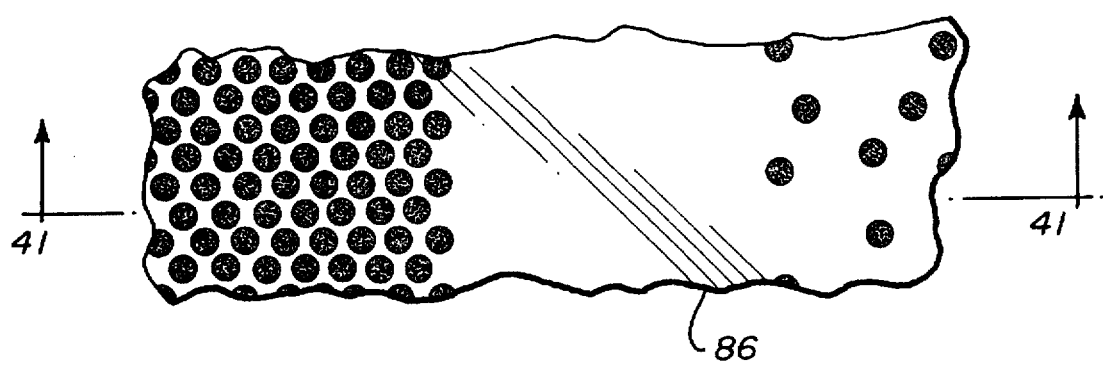
Figure 4I:
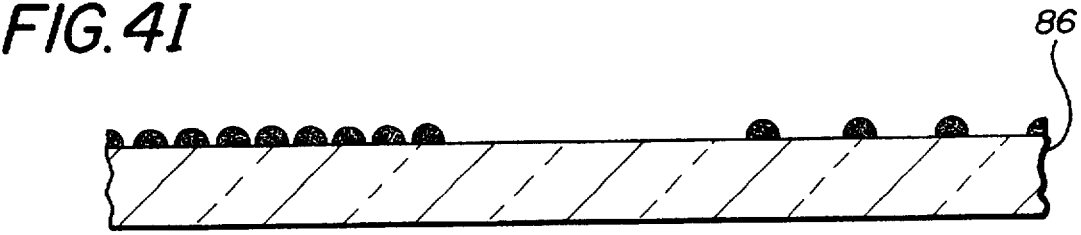
Figure 4J:
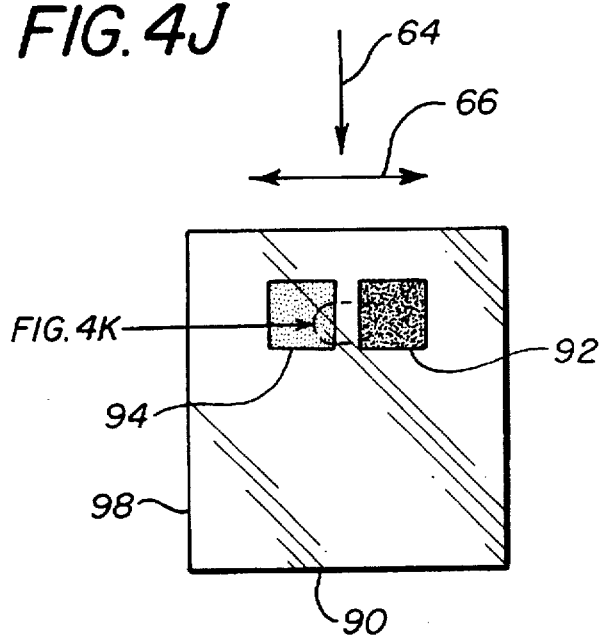
Figure 4K:
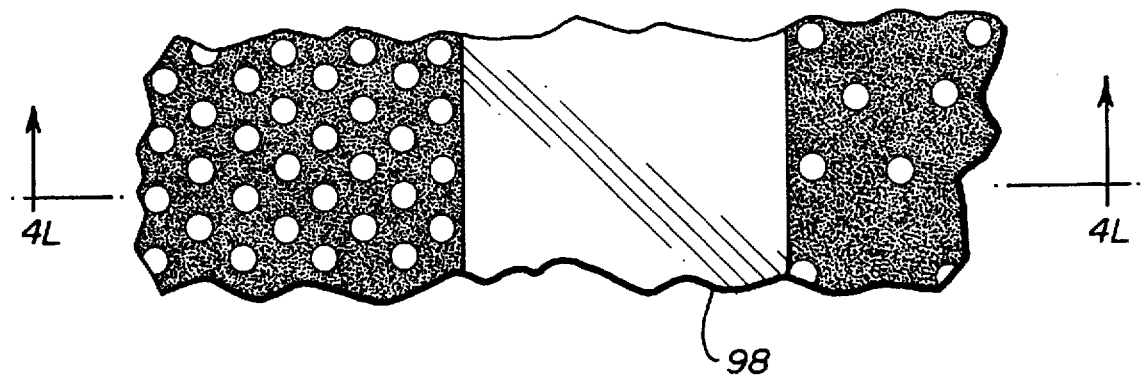
Figure 4L:
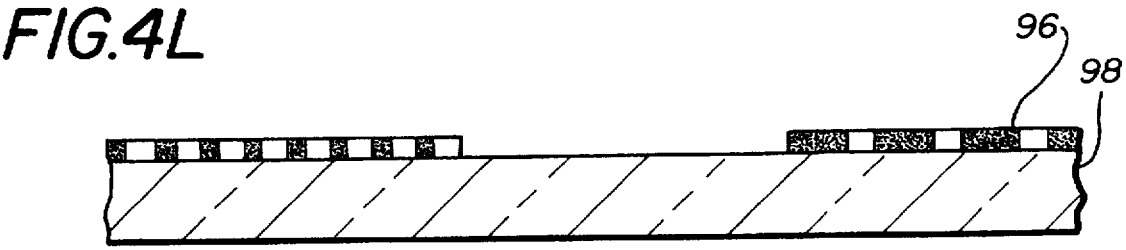
Figure 4M:
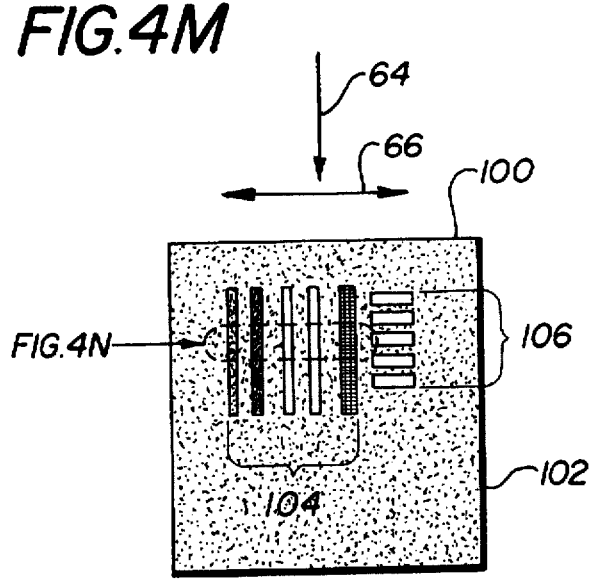
Figure 4N:
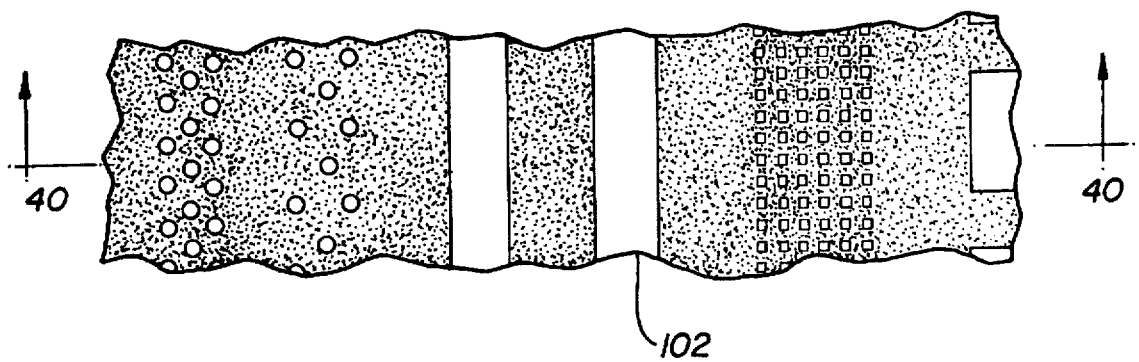
Figure 4O:
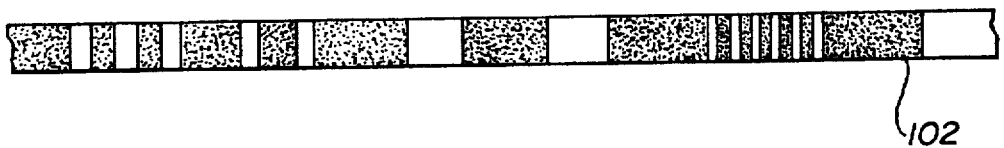

FIGS. 4A through O are front, top and sectional views through different thin-film phantoms which show regions of precisely controlled sub-resolvable scatterers which may be of different density, number of layers, materials, etc. all in accordance with different embodiments of the invention.

FIGS. 5A through L are diagrams of different thin-film phantoms which have different patterns of regions of sub resolvable scatterers in accordance with the invention.

Figure 6:
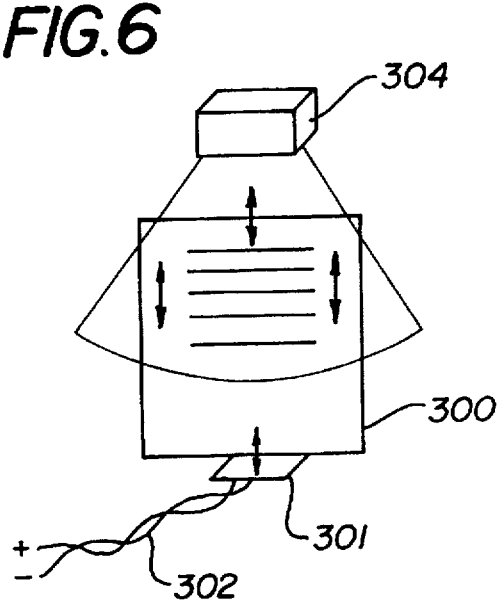
Figure 7:
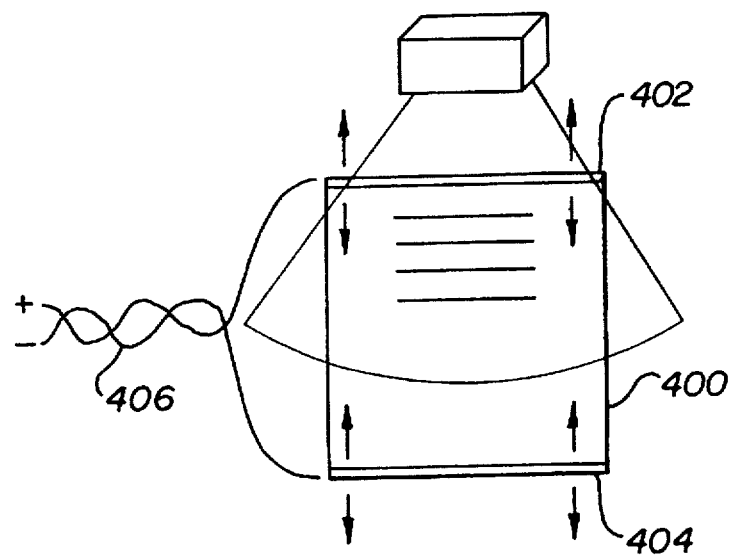

FIG. 6 is a schematic diagram illustrating a system whereby a thin-film phantom in accordance with the invention may be precisely displaced to provide Doppler information;

FIG. 7 is a schematic diagram similar to FIG. 6 of a system in accordance with the invention using a precisely displaceable thin film phantom having a piezoelectric film substrate.

Figure 8:
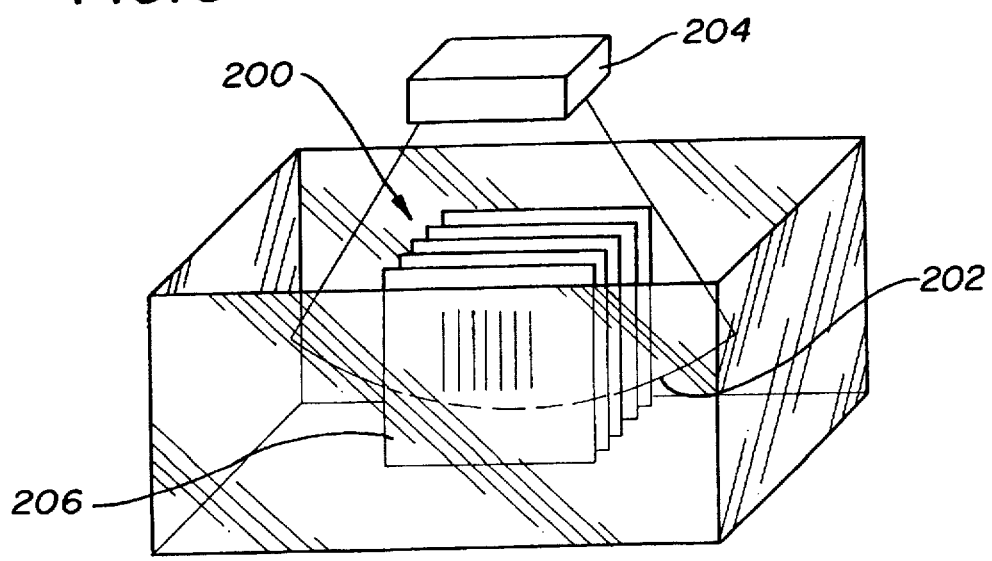

FIG. 8 is a schematic diagram of a system in accordance with the invention utilizing a multiplicity of thin-film phantoms.

Figure 1:
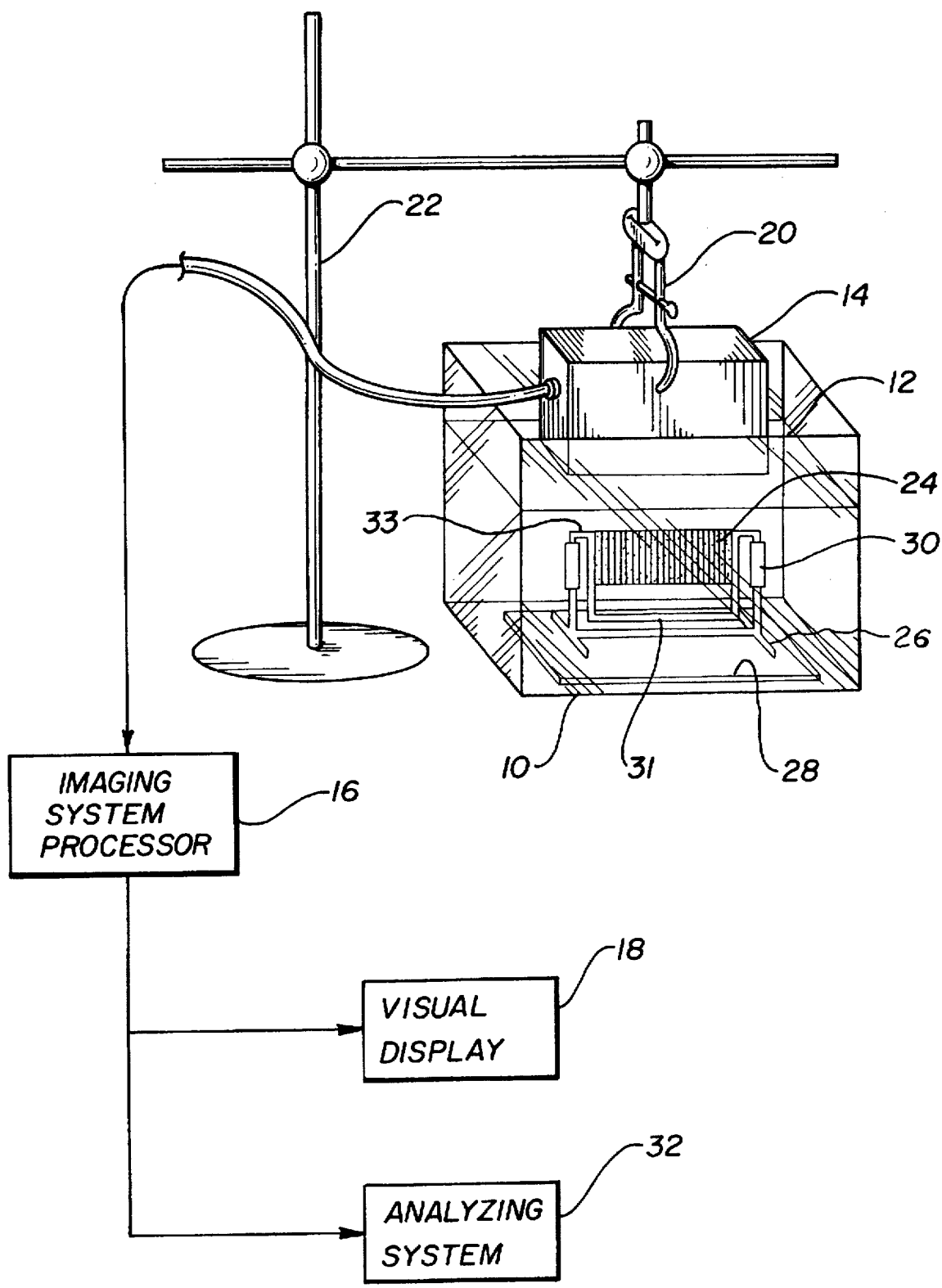
FIG. 1 is a perspective view schematically illustrating the apparatus of an ultrasonic testing system incorporating the invention.

Referring to FIG. 1, there is shown a tank 10 which is filled with a tissue mimicking fluid, gel or medium to a fluid level line 12 which is in the plane of the surface of the medium in the tank 10. In one case, the medium used was water. A medical ultrasound imaging system, which may be of the commercially available type includes an ultrasound transducer 14 and an imaging system processor 16 and a visual display 18. The transducer transmits and receives the ultrasonic beam and is held adjustably by a clamp 20 on a stanchion which is provided by a ring stand 22. The ring stand and clamp are adjustable universally and locate the transducer so that the ultrasonic beam projects into and scans a plane from left to right as shown in FIG. 1. The bottom surface of the transducer is at and in the plane of the water line 12, much in the same way as its transducer would be located on the surface of the skin of the patient during ultrasonic scanning operation.

The beam scanning plane is arranged by adjusting the position of the transducer so that it is coincident with the plane in which a thin film phantom 24 is located. The beam has a width or thickness in which the phantom 24 lies; preferably generally centrally located within the thickness of the beam. The phantom 24 is mounted in a U-shaped frame 33 so that it is maintained rigidly. The frame may be attached to a support bracket 26 which is seated on a plate of sound absorbing material 28 on the bottom of the tank 10. A frame clip 30 may be used to replaceably attach the phantom 24 to the bracket. This facilitates changing phantoms having different target patterns in the testing system.

The testing system also includes an analyzing system 32 which analyzes the video signal which is provided by the imaging system processor to the display 18. The analyzing signal may be of the type which is used to obtain measurements of imaging science criteria such as MTF, spatial frequency resolution, etc. Then the testing system operates in a real time on-line basis. Real time operation can also be provided where the analyzing system 32 has a camera or video frame grabber or digital compression (DICOM) data acquisition system, which obtains the image of the pattern provided by the phantom 24 for analysis by the analyzing system. Alternatively, the analyzing system may be operated off-line and derive information from analysis via a camera input which obtains video information from a photograph of the display obtained by the ultrasonic scanner under test or via a recorded video tape of the same. Alternatively, the analyzing system 32 may be an experienced human observer assessing a predetermined test pattern image for the limits of resolvability of lines, characters, or other echogenic regions formed into image science test patterns. The image for analysis may be data in memory of the processor 16 which is accessed by the analyzing system 32.

The thin-film material of the phantom which provides the insonated material has acoustic impedance close to that of the propagating medium approximates the acoustic impedance of human tissue of which ultrasonic images are made in medical ultrasound operation. Since the thin film or substrate on which the pattern providing the phantom 24 is deposited has an acoustic impedance relatively close to that of the propagating medium, in the tank 10, it should not be visualized on the display 18. The material forming the thin film pattern has a detectably different acoustic impedance than either the substrate of the phantom or the propagating medium. The pattern shown in FIG. 1 is a plurality of side-by-side vertical lines, and is only one pattern of many which may be used. The pattern selected depends upon the imaging science criteria to be analyzed. The pattern generally is a 2D pattern (2-dimensional) in the scanning plane of the beam from the transducer 14.

Generally, the pattern is made by thin film deposition techniques which provide known and even thicknesses of material on the substrate. The substrate itself is preferably of known and constant dimensions. The patterns may be deposited of uniform consistency or in layers so as to have different consistency.

The particles contained in the pattern are sub-resolvable at the wavelength of the ultrasonic energy. The regions containing the patterns are resolvable. Since the actual scatterers are sub-resolvable, the ultrasound system can only detect their presence or absence, not any variability of the exact number and exact position of individual scatterers. The individual scatterers may be referred to as "digital" (either on or off, there or not there) in nature. The precise placement of these digital scatterers can then be used to create regions of controllable echogenicity based on their number per unit area and their arrangement relative to each other, similar in concept to a half-tone printing process. The scattering effectively determines the echogenicity of the regions. The intensity of the reflected energy depends upon the scattering strength which is precisely controlled by the pattern deposition techniques. Half-tone techniques may be used for the purpose of providing a scattering analog of the visual grey scale on the display 18.

By way of example of subresolution scatterers, for a diagnostic medical scanner with a 5 MHz transducer in soft tissue, one wavelength corresponds to approximately 300 microns. One micron features can easily be produced with conventional semi-conductor manufacturing techniques. A generally commercially available 300 dpi (dots per inch) laser printer may be used to print the regions of subresolution scatterers using 10 micron toner particles. The subresolution scatterers produced with such particles may be approximately 85 microns (i.e. dots or features) having maximum diameter of about 85 microns. Such features are sub-resolvable in terms of the wavelength of the ultrasound beam. Thus, in this example even a low cost 300 dpi laser printer can produce sufficiently high resolutions scattering patterns for the purpose of ultrasonic image system evaluation in accordance with the invention.

The pattern may be printed via laser printing on transparencies of acrylic material or Mylar (terylene, plastic) sheets. The patterns may be printed on paper, such as common 20 lb. copier bond paper and transferred to the transparency material, utilizing conventional copier duplicator systems such as the Kodak Ektaprint model 225 printer. Thus, printing directly on the substrate (transparency material) of the phantom 24 with the laser printer or indirectly by transfer to the transparency material may be used.

In one example which is presented here solely for purposes of example, the transparency material was a sheet approximately 7.6 cm. by 12.7 cm. with patterns ranging from 3.8 cm$^2$ to 6.4 cm by 7.6 cm in size. The sheet was placed inside the tank 10. These patterns were placed using the frame shown in FIG. 1 which had a rim 31 which was approximately U-shaped. The frame was made of acrylic and provided a rigidifying support for the phantom 24 as it was imaged. The substrate had a nominal measured thickness of 132 microns. The thickness of the phantom with a pattern was approximately 142 microns, the pattern being approximately 10 microns thick. The edges 33 of the transparency parallel to the face of the transducer 14, from which the beam emanated, was roughened with abrasive material (emery cloth) or cut at random angles, so as to minimize specular reflections and reverberation artifacts from this edge surface.

In this example, the image was captured and stored in the memory of a 386 DX based PC computer equipped with a video acquisition board and video analysis software which provided the analyzing system 32. Also the image was in one test was recorded on video tape and then provided to the PC for analysis.

Figure 2:
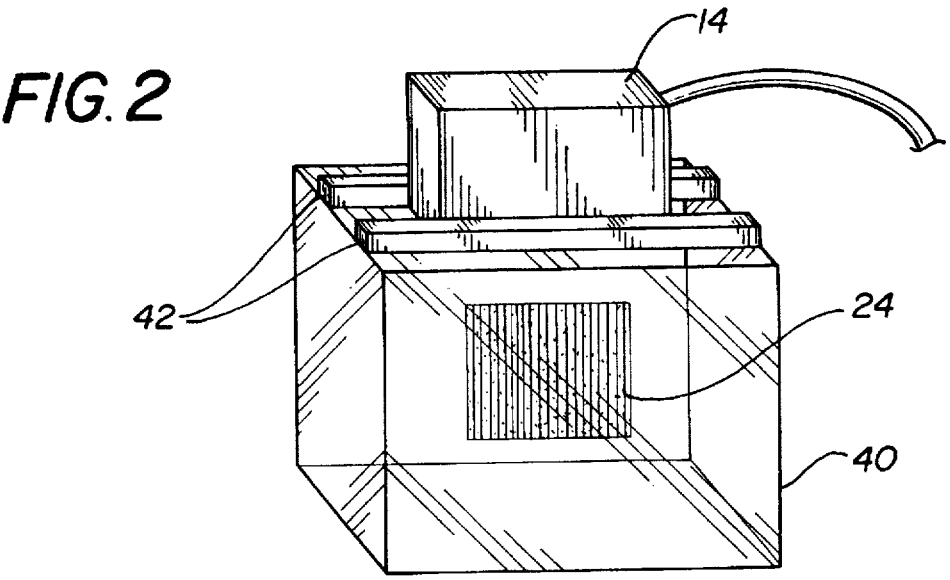
FIG. 2 is a diagram showing a thin film phantom suspended in a tissue mimicking propagation media below the transducer of an ultrasonic imaging system; the phantom being provided in accordance with an embodiment of the invention.

Referring to FIG. 2, there is shown a block 40 containing tissue mimicking material (the propagating medium) in which the thin film phantom is located. Alignment guides 42 on top of the block which themselves are aligned with the plane of the phantom, enable alignment of the transducer 14 of the ultrasound imaging system. The imaging system was evaluated by an imaging system processor and analyzing system such as described in connection with FIG. 1.

Figure 3:
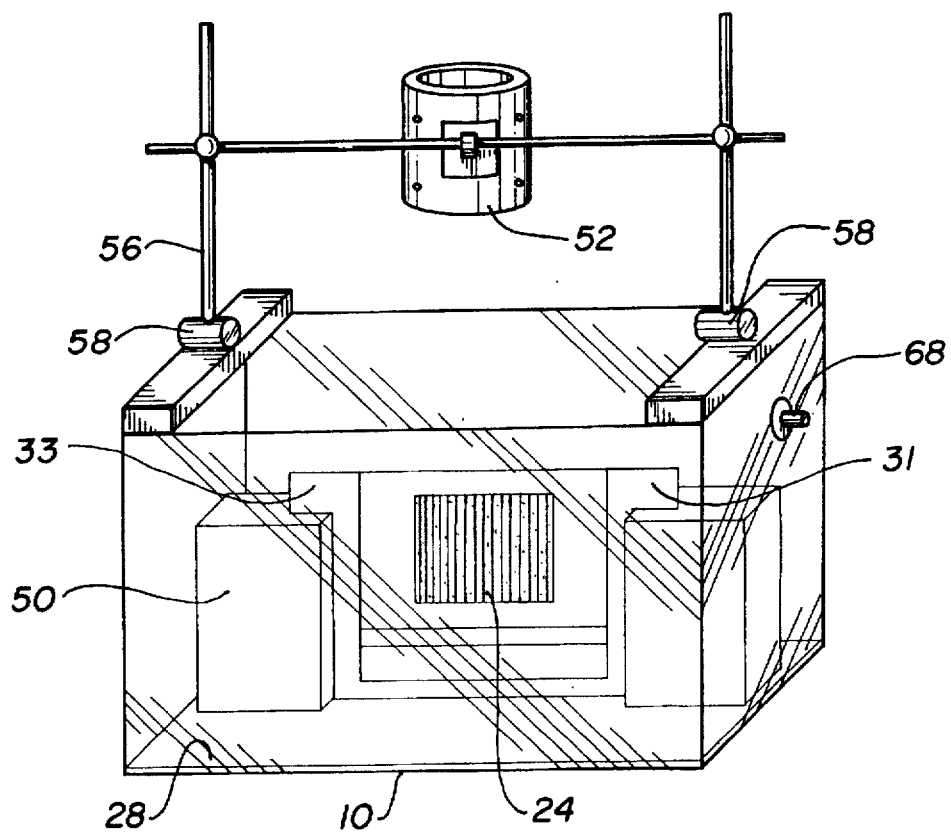
FIG. 3 is a perspective view illustrating schematically the apparatus of a system embodying the invention which utilizes replaceable and vibratable thin-film phantoms.

Referring to FIG. 3, the tank 10 containing the propagating medium (e.g. water) holds the phantom frame 33 in notches in a phantom-insert guide bracket 50 which facilitates interchange of phantoms 24 having different patterns. The transducer 14 (is not shown) but is arranged in a transducer holder 52 which is mounted on a two-sided stand 56 with joints which provide for universal adjustability and alignment of the transducer. The stand 56 may also be tilted about journals 58 and translated along tracks 59 to adjust the offset and angle of the transducer beam with respect to the plane of the phantom 24.

An electrical contact 68 may be provided in order to bring leads through the tank to the phantom for purposes of piezoelectrically displacing the phantom when Doppler measurements are desired as will be explained more fully hereinafter in connection with FIGS. 6 and 7.

FIG. 4A shows the exemplary pattern of parallel equally spaced lines on a thin film or sheet 60 which provides an exemplary phantom 62. FIGS. 4B and C are enlarged fragmentary top and sectional views of the area within the dashed lines on FIG. 4A. The thin film 60 is the substrate on which dots of toner are printed to provide subresolvable scatterers in regions of subresolvable scatterers constituting the two left hand lines of the pattern in FIG. 4A. The subresolvable scatterers (dots) are deposited on the substrate with precisely specified distribution of dots so as to define desired echogenicity when the sheet is insonated by a transducer which projects a beam in the direction of an arrow 64 to insonate the phantom 62. The distribution of dots may be regularly spaced, or may be more unstructured as typically specified by the blue noise mask. The beam may scan laterally across the edge of the phantom in the direction indicated by the double-headed arrow 66.

In FIG. 4D, a front view of another phantom 70 having parallel linear regions forming the pattern on the thin film sheet or substrate 72 is produced by etching a subresolvable voids in a layer 74 of material with a significant acoustic impedance difference from the material of the substrate 72 and the tissue mimicking material (water) which may fill the tank (10—FIG. 1). The layer 74 is etched away completely to form the lines of the pattern. The scattering is produced by etching of subresolvable voids in the layers which form the lines of the pattern. The voids are in a precisely specified and controlled distribution within the regions. The top view of FIG. 4E shows the voids as does the sectional view of FIG. 4F.

FIG. 4G shows a phantom 80 with regions 82 and 84 on the thin film (sheet) substrate 86. These regions have sub-resolvable scatterers which are deposited as by laser printing in the form of dots with precisely defined distributions and spatial density sufficient to produce precisely determined different gray scale levels on the ultrasound imaging system display. The distributions are more apparent from the enlarged top view of FIG. 4H and the sectional view of FIG. 4I.

FIG. 4J is another phantom 90 with regions 92 and 94 which produce significantly different gray scale levels on the ultrasound imaging system display. These regions are formed by etching of a layer 96 of material with a significantly different acoustic impedance from the tissue mimicking material and the material of the thin film sheet 98 on which the patterns are provided by etching the layers to produce distributions of subresolvable voids. The enlarged top view of FIG. 4K and sectional view of FIG. 4L are of the area within the dashed line in FIG. 4J.

FIG. 4M shows a phantom 100 where the thin film (sheet) which provides the substrate 102 is a thin film of a material with acoustic impedance significantly different from the tissue mimicking material and may, for example, be nickel. The phantom 100 has several linear regions 104 and block shaped regions 106 which have precisely placed voids and occlusions such that controlled scattering is produced at the interface between the thin film 102 and the tissue mimicking material (the water in the tank 10—FIG. 1, for example). The top view of FIG. 4N and the sectional view of FIG. 4O are within the dashed lines on FIG. 4M.

Figure 5A:
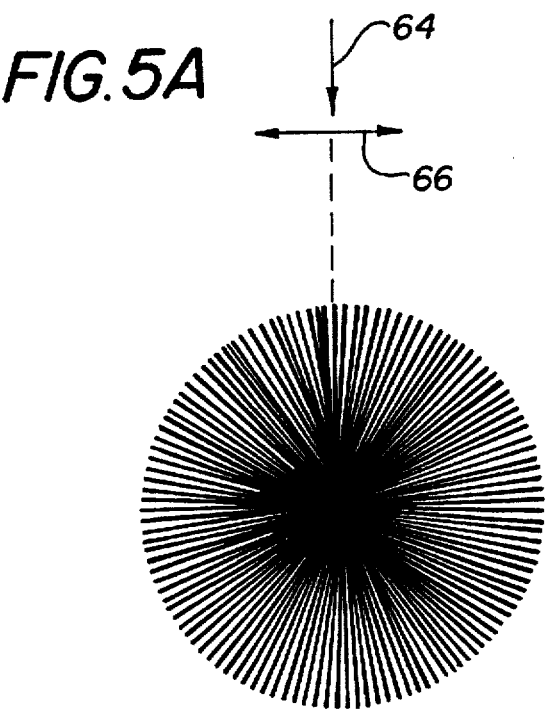

Referring to FIG. 5A, there is shown a pattern of radially disposed regions which forms a star. Such pattern may be used for simultaneously testing axial and lateral resolution, MTF and spatial aliasing imaging science characteristics of the ultrasound imaging system.

Figure 5B:
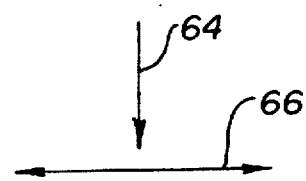
Figure 5B:
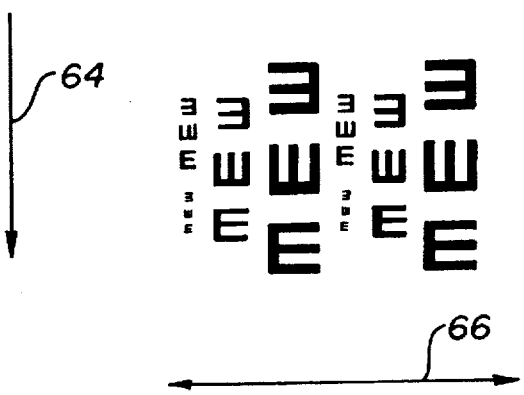

FIG. 5B is a pattern of regions in the form of lateral letter Es. The lateral E pattern primarily characterizes lateral performance at varying depths in the direction of propagation of the ultrasonic beam 64.

Figure 5C:
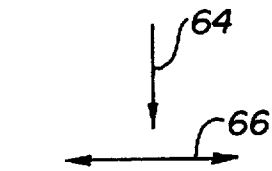
Figure 5C:

FIG. 5C is a pattern of axial Es. This axial E pattern characterizes axial performance over the lateral extent which the beam 64 scans in the direction 66.

Figure 5D:
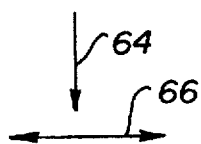
Figure 5D:
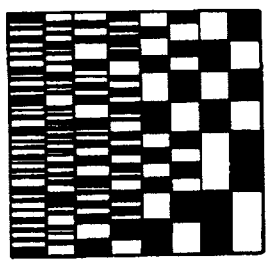
Figure 5E:
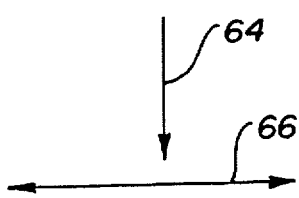
Figure 5E:
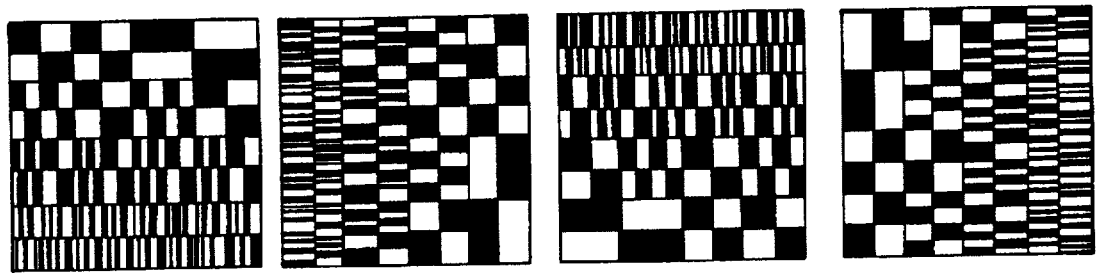

FIGS. 5D and E are single and multiple checkerboard patterns, respectively. These patterns may be used with the transducer producing the beam pattern 64 projecting in the axial direction as shown or laterally from the left or right or even from the bottom thus providing four orthogonally rotated images which can be observed side by side for simultaneous characterization of aliasing, resolution and frequency response.

Figure 5F:
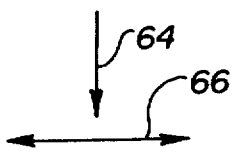
Figure 5F:
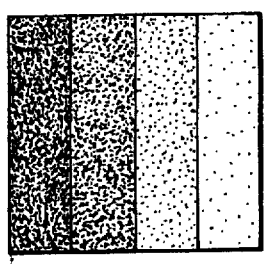

FIG. 5F shows a pattern of four regions constituting blue noise mask (BNM) halftone patterns at 13% and 37% threshold and inverse 13 and 37% thresholds. The blue noise masks may be oriented vertically (in the axial direction) as shown or may be rotated 90° either to the right or to the left. The changing density with depth allows characterization of TGC (time gain compensation) performance of the ultrasonic imaging system.

Figure 5G:
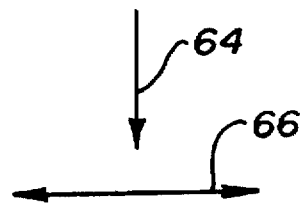
Figure 5G:
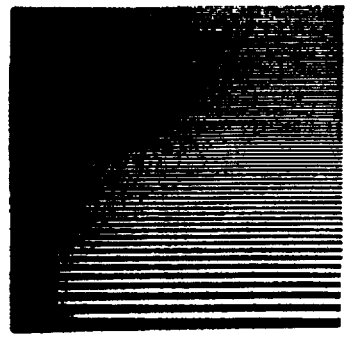

FIG. 5G shows an axial "chirp" pattern with a sinusoidal variation of scatterer density at increasing spatial frequency. The pattern may be rotated 180° so as to decrease the spatial frequency of the chirp with increasing depth.

Figure 5H:
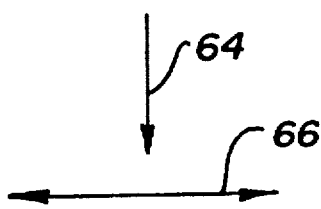
Figure 5H:
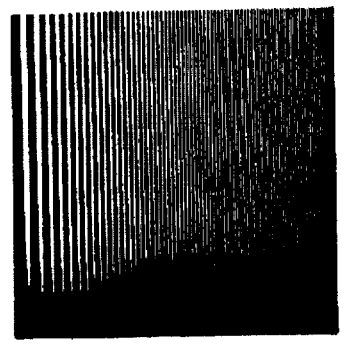

FIG. 5H shows a lateral "chirp" pattern with sinusoidal variation of scatterer density at increasing spatial frequency. It is shown oriented with increasing contrast from top to bottom (with axial depth). The contrast variation within a given cycle is due to the change in subresolvable scatterer density in the pattern.

Figure 5I:
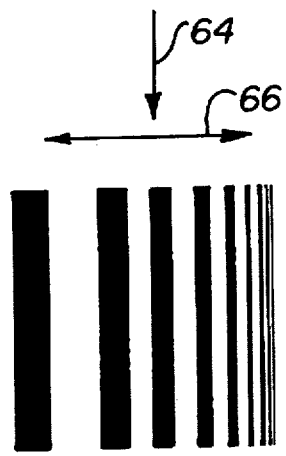
Figure 5J:
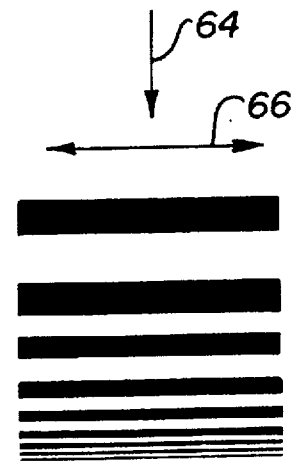
Figure 5K:
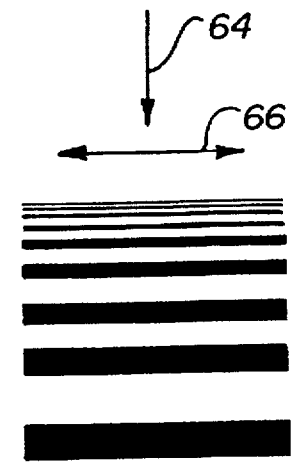

FIGS. 5I, J and K show different line pair chirp patterns for lateral and axial chirps. FIG. 5J shows the axial chirp with spatial frequency increase with depth, while FIG. 5K shows the axial chirp with decreasing spatial frequency with depth.

Figure 5L:
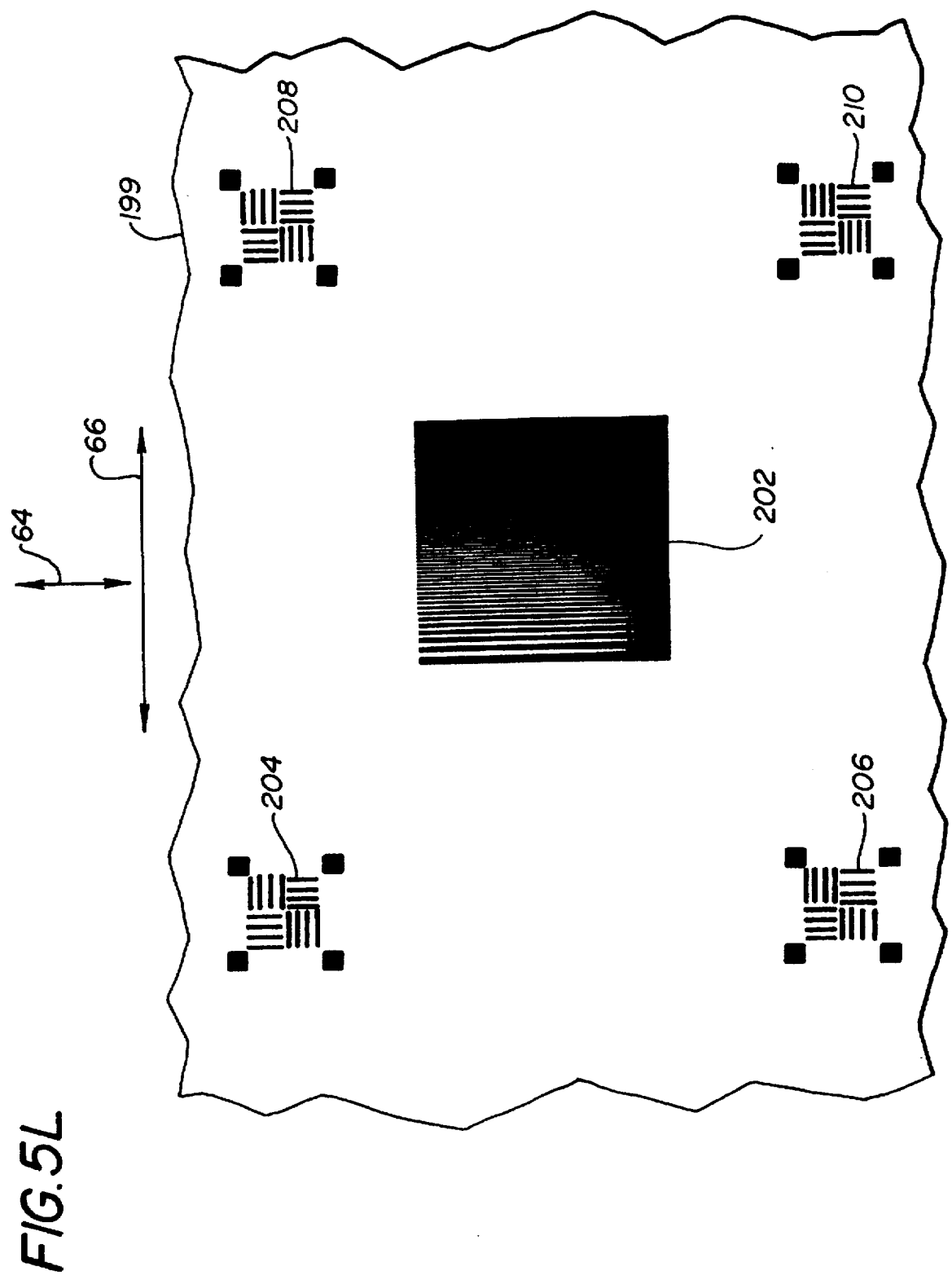

Referring to FIG. 5L there is shown a phantom 199 line pair "chirp" pattern 202 with secondary square and line patterns 204–210 located adjacent to the pattern 202 for alignment purposes. If transducer is properly aligned with plane of primary pattern 202 with time-gain compensation in the ultrasonic imaging system, the four secondary patterns 204–210 are displayed with similar intensity on the displayed image. Thus indicating that the phantom 198 is aligned with the beam 64 as it scans in the lateral directions 166.

FIGS. 6 and 7 show, schematically, how a thin film target may be precisely displaced as by being vibrated. The thin film target is a phantom 300 in FIG. 6 to which is attached a film of piezoelectric material such as PVDF 301 to which electrodes are connected by leads 302. The transducer 304 insonates the phantom 300 and obtains an image containing Doppler (velocity) information (the rate of vibration of the phantom 300).

FIG. 8 schematically illustrates a multiplicity of thin film targets or phantoms 200 in a tank submerged in a propagating medium (e.g., water). The interrogating ultrasonic beam scans laterally from left to right and axially along the planes of the sheets. The transducer 204 may be moved in a direction perpendicular to the lateral direction of the sweep of the beam from the transducer indicated by the arc 202 so as to allow measurement of beam thickness in the elevation axis and its effects on the displayed image.

A phantom 400 as shown in FIG. 7, is a sheet of piezoelectric film, such as PVDF with electrodes 402 and 404 deposited along its edges. A varying electrostatic field is applied across the phantom 400 via leads 406 and displaces the sheet with its pattern (the phantom—400) in the axial direction. Such displacement may have a sinusoidal vibration and provide an image containing Doppler (velocity) information.

With both the embodiments of FIGS. 6 and 7, the doppler performance of the ultrasonic imaging system may be tested including continuous wave Doppler (velocity) pulsed wave Doppler (velocity) and color Doppler (velocity) imaging modes.

From the foregoing description, it will be apparent that there has been provided improved thin film phantoms and phantom systems. These phantom systems have regions of patterns in various forms and arrangements in addition to those described in the foregoing specification. Such other patterns and regions as well as variations and modifications in the phantoms themselves, will undoubtedly suggest themselves to those skilled in the art. Accordingly, the foregoing specification and description should be taken as illustrative and not in a limiting sense.

We claim:

1. A method of testing ultrasonic imaging systems which systems project a beam having a thickness which beam scans a plane to form an image of objects in the plane which objects reflect the beam to produce resolvable echoes when the objects are of a size resolvable by said beam, said method comprising the steps of providing regions with a precisely arranged pattern of regions of sub-resolvable scatterers in a layer on a planar medium, said medium being of thickness less than the thickness of said beam, through which medium said beam propagates in the plane of the medium without substantial reflection or attenuation by the medium, and analyzing an image formed by said pattern to evaluate the performance of said systems.

2. The method according to claim 1 wherein said analyzing step is carried out to evaluate performance as manifested by characteristics selected from the group consisting of distortion, aberrations, imaging artifacts, spatial frequency response, modulation transfer function (MTF), aliasing, and resolution limits.

3. The method according to claim 1 wherein said analyzing step is carried out to calibrate said ultrasonic imaging systems.

4. The method according to claim 1 wherein said sub-resolvable scatterers are digital scatterers and said regions are the only areas of said medium which constitute echogenic regions of resolvable size.

5. The method according to claim 1 wherein said step of providing said pattern is carried out to produce said regions with precisely controlled ultrasound scattering properties.

6. The method according to claim 5 wherein said precisely controlled scattering properties are obtained by selecting sizes and distribution of said sub-resolvable scatterers in said regions.

7. The method according to claim 5 wherein said regions of precisely controlled scattering properties are formed by a step selected from the group consisting of electrostatically printing, etching, photo-lithographic printing, sputtering and vacuum deposition, with material having an acoustic impedance detectably different from the material of said planar medium, and etching of said planar medium.

8. A method of testing ultrasonic imaging systems which systems project a beam which beam scans a plane to form an image of objects in the plane which objects reflect the beam to produce detectable echoes when the objects are of a size resolvable by said beam, said method comprising the steps of providing regions with a precisely arranged pattern of sub-resolvable scatterers on a planar medium without substantial reflection by the medium, analyzing an image formed by said pattern to evaluate the performance of said systems, wherein said step of providing said pattern is carried out to produce said regions with precisely controlled ultrasound scattering properties, and wherein said regions of precisely controlled scattering properties are formed by xerographic printing of said regions and is carried out with the aid of a laser printer.

9. The method according to claim 5 wherein said regions of precisely controlled scattering properties are formed by producing half-tones in said regions thereby providing an image having selectable grey scales.

10. The method according to claim 9 wherein said halftones are printed via a halftone threshold array mask.

11. The method according to claim 10 wherein said mask is a blue noise mask.

12. The method according to claim 9 wherein said halftone regions are printed via a computer-generated half-tone screen.

13. The method according to claim 12 wherein said computer generated screen produces a blue noise pattern of selected density.

14. The method according to claim 1 wherein said planar medium is a thin film or sheet substrate on which said pattern is disposed.

15. The method according to claim 1 wherein said medium consists of tissue mimicking material.

16. The method according to claim 14 wherein said substrate is a thin film sheet of material selected from the group consisting of PVDF, acrylic and terylene plastic.

17. The method according to claim 14 wherein said providing step includes the step of maintaining said substrate in a plane oriented generally in the direction of propagation of said beam of ultrasonic energy.

18. The method according to claim 5 wherein said precisely controlled scattering properties are obtained by selecting at least one characteristic of said regions from the group consisting of the density of said sub-resolvable scatterers, the number of sub-resolvable scatterers per unit area, the thickness of said scatterers in a direction transverse to said plane of the medium, the acoustic impedance of said scatterers, materials of said medium having selected sound propagating characteristics, selected numbers of layers of said sub-resolvable scatterers, and the size of particles forming said scatterers.

19. The method according to claim 1 wherein said pattern providing step is carried out by arranging said regions as unstructured patterns of subresolvable scatterers on said medium corresponding to a constant spatial frequency spectrum from which broadband response characteristics of said systems can be evaluated when said analyzing step is carried out.

20. The method according to claim 1 wherein said pattern providing step is carried out by arranging said regions as a regular or periodic pattern of subresolvable scatterer regions to enable evaluation of frequency dependent characteristics of said ultrasonic imaging systems when said analyzing step is carried out.

21. The method according to claim 1 wherein said pattern providing step is carried out by arranging said pattern as a chirp pattern of areas in the form of bars of progressively varying width and spacing to enable evaluation of the MTF characteristic of said systems when said analyzing step is carried out.

22. The method according to claim 1 wherein said pattern providing step is carried out by repeating like arrangements of said regions at different depths in an axial direction which is the general direction of propagation of said beam.

23. The method according to claim 1 wherein said beam is provided in repetitive pulses of ultrasonic energy at certain repetitive rate and further comprising the step of displacing said medium and pattern, thereby enabling the evaluation of the performance of said systems in making Doppler (velocity) measurements during said analyzing step.

24. The method according to claim 23 wherein said medium is a sheet of piezoelectric material and said displacing step is provided by producing a varying electrical field across said sheet.

25. The method according to claim 24 wherein said electrical field producing step is carried out by varying said field sinusoidally.

26. The method according to claim 1 wherein information representing said image is transmitted over a communications link to a receiving station, and said analyzing step is carried out at said receiving station thereby enabling ultrasonic imaging systems operative via teleradiography links to be evaluated in said systems entirety.

27. The method according to claim 1 wherein said pattern providing step is carried out to provide a second pattern located adjacent to said pattern of regions of sub-resolvable scatterers and further comprising the step of aligning said beam with said medium utilizing said second pattern.

28. The method according to claim 1 further comprising the step of arranging a plurality of planar mediums having patterns provided by said pattern providing step in side by side relationship with the planes of said mediums oriented in an axial direction which is generally along the direction of propagation of said beam.

29. A phantom for testing ultrasonic imaging systems comprising a planar medium through which medium a beam of ultrasonic energy propagates in the plane of the medium without substantial reflection or attenuation by the medium, said planar medium having a thickness less than the thickness of said beam, and a layer providing regions with a precisely arranged pattern of sub-resolvable scatterers on a surface of said medium for testing said systems.

30. The phantom according to claim 29 wherein said regions are the only areas of said medium having digital scatterers and which are echogenic.

31. The phantom according to claim 30 wherein said scatterers are sized and distributed such that said regions have precisely controlled ultrasound scattering properties, and are of resolvable size.

32. The phantom according to claim 31 wherein the areas of said regions provide said precisely controlled scattering properties.

33. The phantom according to claim 31 wherein said regions of precisely controlled scattering properties are printed or etched from a layer of material having an acoustic impedance detectably different from an environment in which said phantom is disposed.

34. The phantom according to claim 31 wherein said regions of precisely controlled scattering properties define said pattern as half-tones thereby providing images having selectable grey scales.

35. The phantom according to claim 34 wherein said half tones are blue noise mask derived patterns.

36. The phantom according to claim 29 wherein said planar medium is a thin film or sheet substrate on which said pattern is disposed.

37. The phantom according to claim 29 wherein said propagating medium consists of tissue mimicking material.

38. The phantom according to claim 36 wherein said substrate is a thin film sheet of material selected from the group consisting of PVDF, acrylic and terylene plastic.

39. The phantom according to claim 36 further comprising means for maintaining said substrate in a plane oriented generally in the direction of propagation of said beam of ultrasonic energy.

40. The phantom according to claim 31 wherein said regions have a characteristic selected, to enable testing of said systems for different imaging science criteria, from the group consisting of the density of said sub-resolvable scatterers in said regions, the number of said sub-resolvable scatterers per unit area, the thickness of said scatterers in a direction transverse to said plane of the medium, the acoustic impedance of said scatterers relative to the acoustic impedance of said medium, the numbers of layers of said sub-resolvable scatterers, and the size of particles forming said scatterers.

41. The phantom according to claim 29 wherein regions of subresolvable scatterers of said pattern are randomly located to define a constant spatial frequency spectrum thereby enabling evaluation of broadband response characteristics of said systems.

42. The phantom according to claim 29 wherein said regions are regular or periodic patterns of subresolvable scatterers of said regions to enable evaluation of frequency dependent characteristics of said ultrasonic imaging systems.

43. The phantom according to claim 29 wherein said regions are bar shaped, and said pattern is a chirp pattern wherein said bars have progressively varying widths and spacings to enable evaluation of the MTF characteristic of said systems.

44. The phantom according to claim 29 wherein said regions are at different spacings from each other in an axial direction which is the general direction of propagation of said beam.

45. The phantom according to claim 29 wherein a second pattern is located adjacent to said pattern of regions of sub-resolvable scatterers which is useful in aligning said beam with said medium.

46. The phantom according to claim 29 further comprising a plurality of planar mediums including said planar medium according to claim 29, having patterns in side-by-side relationship and with the planes of said mediums oriented in an axial direction which is generally along the direction of propagation of said beam.

47. A system comprising a phantom according to claim 29 and wherein said beam is provided in repetitive pulses of ultrasonic energy at certain repetitive rate, and further comprising means for displacing said medium during individual ones of said pulses, thereby enabling the evaluation of the performance of said systems in making Doppler shift (velocity) based measurements and images.

48. The system according to claim 47 wherein said medium is a sheet of piezoelectric material and said displacing means is provided by means for producing a varying electrical field across said sheet.

49. The system according to claim 48 wherein said electrical field producing means includes means for varying said field sinusoidally.

50. A system for quality assurance of an ultrasound imaging system unit in accordance with imaging science criteria which comprises a phantom having regions with a precisely arranged pattern of sub-resolvable scatterers arranged in a layer on the surface of a sheet of ultrasonically transmissive material in an imaging science test pattern, and means for analyzing an image provided by said system for said imaging science criteria.

51. The system according to claim 50 wherein said sheet of phantom is a thin film of a medium transmissive of ultrasound energy in a plane, and said sub-resolvable scatterers are located in regions of resolvable size on said thin film.

52. The system according to claim 50 further comprising means for applying precise displacements to said scatterers such that the quality of said imaging system for Doppler shift and color velocity can be assured.

53. The system according to claim 50 wherein said system is part of an ultrasound teleradiology unit and said analyzing means is remote from said phantom.

* * * * *